US007678054B2

(12) United States Patent
Okazaki et al.

(10) Patent No.: US 7,678,054 B2
(45) Date of Patent: Mar. 16, 2010

(54) ULTRASONIC PROBE AND ULTRASONIC DIAGNOSING DEVICE

(75) Inventors: Hideki Okazaki, Chiba (JP); Mikio Izumi, Saitama (JP)

(73) Assignee: Hitachi Medical Corporation, Tokyo (JP)

( * ) Notice: Subject to any disclaimer, the term of this patent is extended or adjusted under 35 U.S.C. 154(b) by 1268 days.

(21) Appl. No.: 10/543,322

(22) PCT Filed: Jan. 23, 2004

(86) PCT No.: PCT/JP2004/000610

§ 371 (c)(1),
(2), (4) Date: Jul. 25, 2005

(87) PCT Pub. No.: WO2004/064643

PCT Pub. Date: Aug. 5, 2004

(65) Prior Publication Data

US 2006/0142659 A1 Jun. 29, 2006

(30) Foreign Application Priority Data

Jan. 23, 2003 (JP) ............................. 2003-014586

(51) Int. Cl.
*A61B 8/14* (2006.01)
*H01L 41/00* (2006.01)
*B06B 1/06* (2006.01)

(52) U.S. Cl. ........................ 600/459; 310/320; 367/140

(58) Field of Classification Search ................. 600/459; 310/322; 367/140
See application file for complete search history.

(56) References Cited

U.S. PATENT DOCUMENTS 5,212,671 A * 5/1993 Fujii et al. .................. 367/151
5,415,175 A * 5/1995 Hanafy et al. ............... 600/459
6,572,552 B2 * 6/2003 Fukukita ..................... 600/459

FOREIGN PATENT DOCUMENTS

| | | |
|---|---|---|
| JP | 58-45551 | 3/1983 |
| JP | 3-151948 | 6/1991 |
| JP | 5-183995 | 7/1993 |
| JP | 7-107595 | 4/1995 |
| JP | 8-275944 | 10/1996 |
| JP | 2001-25094 | 1/2001 |
| JP | 2001-161689 | 6/2001 |
| JP | 2002-45357 | 2/2002 |

* cited by examiner

*Primary Examiner*—Eric F Winakur
*Assistant Examiner*—Michael T Rozanski
(74) *Attorney, Agent, or Firm*—Antonelli, Terry, Stout & Kraus, LLP.

(57) ABSTRACT

An array of a plurality of ultrasonic transducers having a piezoelectric layer 2 and a couple of electrodes 7-1 and 7-2 sandwiching the piezoelectric layer therebetween is provided. The piezoelectric layer 2 has a first piezoelectric layer 2-1 provided on the ultrasonic-wave emission side, a second piezoelectric layer 2-2 provided on the other side of the first piezoelectric layer 2-1, and a common electrode 8 provided therebetween. Each of the ultrasonic transducers has a low-frequency response distribution that is uniform in the minor-axis direction perpendicular to a direction in which the ultrasonic transducers are arranged and a high high-frequency response distribution at a center part in the minor-axis direction. The characteristics of the minor-axis-direction frequency and sound pressure of the first piezoelectric layer are complemented by those of the second piezoelectric layer, whereby a uniform frequency characteristic for a minor-axis-direction low frequency is obtained.

7 Claims, 10 Drawing Sheets

ULTRASONIC PROBE AND ULTRASONIC DIAGNOSING DEVICE

TECHNICAL FIELD

The present invention relates to an ultrasonic probe for transmitting and receiving an ultrasonic wave between itself and a patient, and an ultrasonic diagnosing apparatus including the probe. More specifically, the present invention relates to an ultrasonic probe that can change an aperture in the minor-axis direction.

BACKGROUND ART

In general, an ultrasonic transducer includes a pair of electrodes sandwiching a layer including a piezoelectric material (hereinafter referred to as a piezoelectric layer), and an ultrasonic probe includes a plurality of the ultrasonic transducers, where the ultrasonic transducers are one-dimensionally arrayed, for example. Further, a predetermined number of transducers of the transducers arrayed in the major-axis direction are determined to be an aperture, the plurality of transducers belonging to the aperture is driven, and an ultrasonic beam converges to a part to be measured in a patient so that the part is irradiated with the ultrasonic beam. Further, the plurality of transducers belonging to the aperture receives an ultrasonic reflective echo or the like emitted from the patient and the ultrasonic reflective echo is converted to an electrical signal.

On the other hand, as for the minor-axis direction perpendicular to the above-described major-axis direction, an aperture-width is modified by changing the frequency of an ultrasonic wave so that the beam-width of the ultrasonic beam decreases and the resolution increases (Patent Document 1: JP7-107595A). In an ultrasonic probe according to Patent Document 1, the thickness of a piezoelectric layer at the center in the minor-axis direction is small and gradually increases toward the end thereof. Therefore, the response to a high frequency at the center is high and the response to a low frequency at the end in the minor-axis direction is high, so that a wide-band frequency characteristic is obtained. As a result, the aperture-width in the minor-axis direction of the ultrasonic probe varies inversely with a frequency, whereby a fine beam-width is achieved over an area ranging from a shallow depth to a deep depth.

However, according to the ultrasonic probe disclosed in Patent Document 1, the low-frequency responses at both ends in the minor-axis direction become higher than that at the center part and the sound pressure at each of the ends is higher than that at the center part, whereby a nonuniform sound-pressure distribution is obtained. Subsequently, the resolution of the ultrasonic probe decreases.

DISCLOSURE OF INVENTION

The present invention has been achieved for making the frequency response of an ultrasonic probe to a minor-axis-direction frequency uniform.

The present invention solves the above-described problems through the following means.

According to the present invention, in an ultrasonic probe including an array of a plurality of ultrasonic transducers, where each of the ultrasonic transducers has a piezoelectric layer and a couple of electrodes sandwiching the piezoelectric layer therebetween, the piezoelectric layer has a first piezoelectric layer provided on the ultrasonic-wave emission side, a second piezoelectric layer provided on the other side of the first piezoelectric layer, and a common electrode provided therebetween. The ultrasonic probe has a low-frequency-response distribution that is uniform for an entire aperture in the minor-axis direction perpendicular to a direction in which the ultrasonic transducers are arrayed and a high-frequency-response distribution that is high at the center part in the minor-axis direction.

The above-described frequency-response distributions can be achieved by the following means shown in (1) to (9).

(1) The thickness of the end in the minor-axis direction of the first piezoelectric layer is smaller than the thickness of the center part of the first piezoelectric layer and the thickness of the end of the second piezoelectric layer is larger than the thickness of the center part of the second piezoelectric layer, (2) each of faces of the first and second piezoelectric layers, the faces being in contact with the couple of electrodes, is plane and a boundary surface between the first piezoelectric layer and the second piezoelectric layer is formed, as a curved face depressed to the second-piezoelectric-layer side, (3) each of the faces of the first and second piezoelectric layers, the faces being in contact with the couple of electrodes, is plane and the boundary surface between the first piezoelectric layer and the second piezoelectric layer is formed, as a crest whose ridge line corresponds to the center part in the minor-axis direction, (4) each of the faces of the first and second piezoelectric layers, the faces being in contact with the couple of electrodes, is plane and the boundary surface between the first piezoelectric layer and the second piezoelectric layer has a plane part that is provided at the center part in the minor-axis direction and that is projected to the second-piezoelectric-layer side, and a plane part that is provided at each of both the ends, where the plane parts are projected to the first-piezoelectric-layer side, (5) the face of the first piezoelectric layer on the ultrasonic-wave emission side is concave, the face of the second piezoelectric layer on the ultrasonic-wave non-emission side is convex, and the boundary surface between the first piezoelectric layer and the second piezoelectric layer is depressed to the second-piezoelectric-layer side with a curvature larger than the curvature of the face of the first piezoelectric layer on the ultrasonic-wave emission side, (6) the face of the first piezoelectric layer on the ultrasonic-wave emission side is concave, the face of the second piezoelectric layer on the ultrasonic-wave non-emission side is convex, and the boundary surface between the first piezoelectric layer and the second piezoelectric layer is formed, as the crest whose ridge line corresponds to the center part in the minor-axis direction, (7) each of the first and second piezoelectric layers has a predetermined thickness, where the density of a piezoelectric material used for the first piezoelectric layer decreases from the center part in the minor-axis direction toward the end, and where the density of a piezoelectric material used for the second piezoelectric layer increases from the center part in the minor-axis direction toward the end, and (8) in addition to the configuration shown in (1) to (7), an adjustment layer including a material whose acoustic impedance is nearly equivalent to the acoustic impedance of the piezoelectric material used for the piezoelectric layer is provided on the ultrasonic-wave non-emission side of the second piezoelectric layer, where the thickness in the minor-axis direction of the adjustment layer gradually increases from the center part to the end.

According to the above-descried (1) to (7), the piezoelectric layer includes two layers and the minor-axis-direction frequency characteristic and sound-pressure characteristic of the first piezoelectric layer and those of the second piezoelectric layer complement one another. Subsequently, responses to low frequencies in the minor-axis direction are made uniform. That is to say, the thickness of the second piezoelectric layer gradually increases from the center part thereof in a direction perpendicular to a direction in which the ultrasonic transducers are arrayed (hereinafter referred to as a minor-axis direction) toward the ends. Therefore, the high-frequency response at the center part becomes high. On the other hand, the thickness of the first piezoelectric layer decreases from the center part in the minor-axis direction toward the ends, so that the low-frequency response at the center part becomes high. Since the frequency-response characteristic of the first piezoelectric layer is added to that of the second piezoelectric layer, the minor-axis-direction response characteristic for a low frequency becomes uniform. Subsequently, according to the ultrasonic probe of the present invention, it becomes possible to obtain a high response to a high frequency at the center part in the minor-axis direction of the transducers and a uniform low-frequency response for each of the entire aperture, whereby it becomes possible to obtain a small ultrasonic beam-width over an area ranging from a small depth to a large depth, so that a high resolution is achieved.

Further, since the acoustic impedance of the adjustment layer according to configuration (8) is nearly equivalent to that of the piezoelectric material, there is a large difference between the acoustic impedance of the adjustment layer and that of the backing layer provided on the anti-piezoelectric-layer side of the adjustment layer. Subsequently, an ultrasonic wave is effectively reflected by the adjustment layer and the frequency characteristic of the reflective ultrasonic wave depends on the thickness. As a result, the response characteristic in the minor-axis direction of the transducer for a low frequency becomes more uniform than in the past. Further, a high-frequency component of an ultrasonic wave emitted from the transducer to the back-face side is reflected by the adjustment layer that is thin at the center of the transducer and transmitted back to the ultrasonic-wave emission side. Subsequently, the sound pressure of a high frequency emitted from the center of the ultrasonic probe in the minor-axis direction to the patient increases, whereby a high-frequency response is obtained at the center of the transducer in the minor-axis direction.

Here, the backing layer includes a material whose acoustic impedance is significantly smaller than that of the piezoelectric layer. Further, the attenuation rate of the material is higher than that of the piezoelectric layer. Subsequently, it becomes possible to change the frequency characteristic in the minor-axis direction and achieve the function for changing an aperture according to a frequency. Further, the distribution of the thickness of the adjustment layer in the minor-axis direction is determined to be a frequency characteristic for achieving a predetermined high-frequency response distribution.

In place of the above-described configurations (1) to (8), there is provided configuration (9), wherein each of the first and second piezoelectric layers has a predetermined thickness, the adjustment layer including the material whose acoustic impedance is nearly equivalent to the acoustic impedance of the piezoelectric material used for the piezoelectric layer is provided on a back face of the electrode in contact with the second piezoelectric layer, and the thickness of the adjustment layer gradually increases from the center part of the ultrasonic transducer in the minor-axis direction toward the end.

Since the above-described adjustment layer is provided, the response characteristic for a low frequency in the minor-axis direction of the transducer becomes uniform and a high high-frequency response can be obtained at the center of the transducer in the minor-axis direction, as described above.

Further, the ultrasonic diagnosing apparatus of the present invention uses the ultrasonic probe of the present invention. Transmission means for transmitting an ultrasonic signal for driving the transducers of the ultrasonic probe has the function of transmitting an ultrasonic signal with a frequency according to a control instruction to the ultrasonic probe. A reception-processing means for performing reception processing for a reflective-echo signal received by the ultrasonic probe has the function of selecting a reflective-echo signal with the frequency according to the control instruction and performing the reception processing. Subsequently, a high-frequency response can be obtained at the center of the transducer in the minor-axis direction. Further, since the response characteristic for a low frequency in the minor-axis direction becomes uniform, it becomes possible to obtain the small ultrasonic beam-width over the area ranging from a small depth to a large depth and achieve the high resolution.

BEST MODE FOR CARRYING OUT THE INVENTION

Embodiments of the present invention will be described with reference to the attached drawings, as below.

First Embodiment

Figure 1:
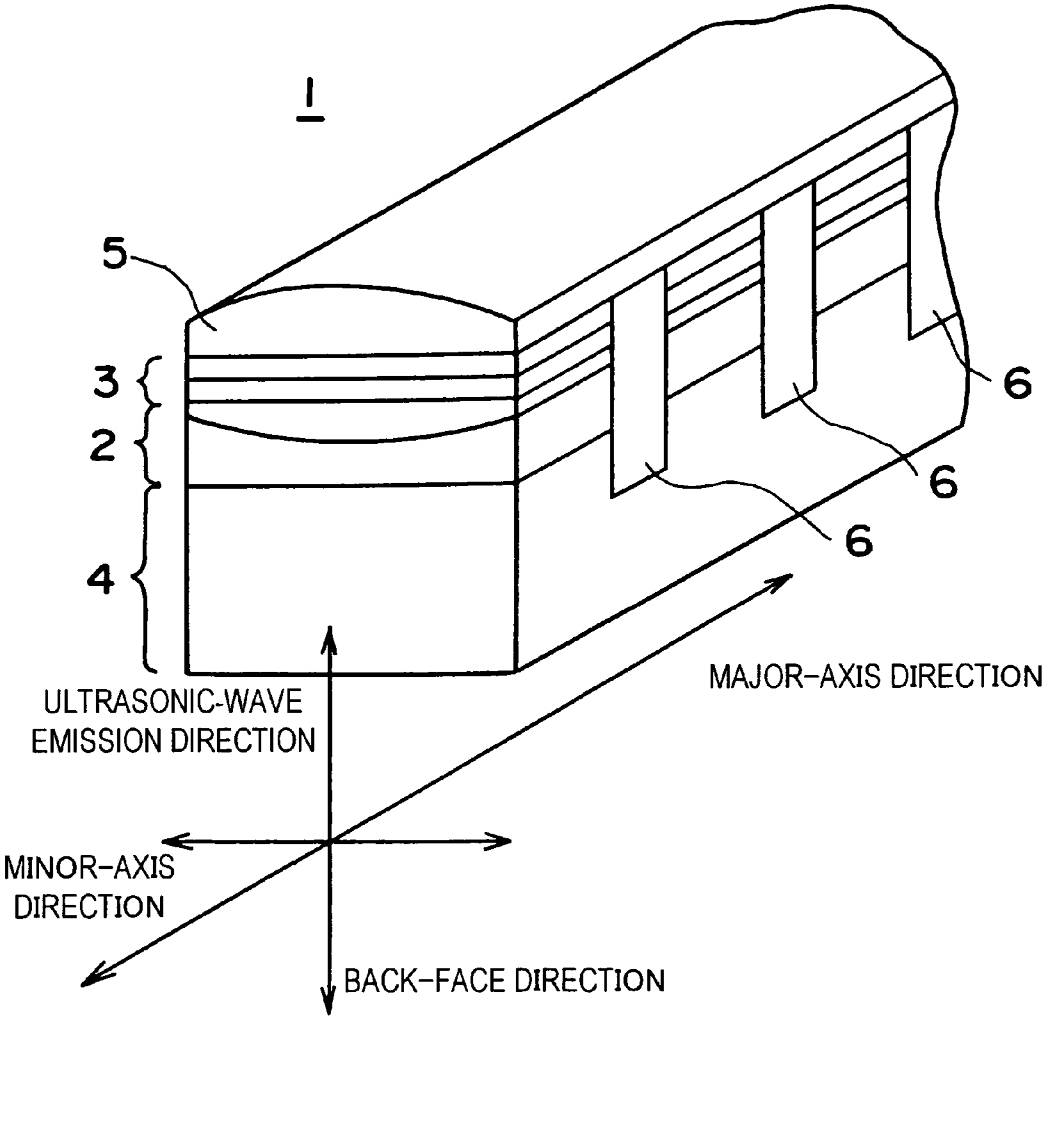
FIG. 1 is a perspective view of main part of an ultrasonic probe according to an embodiment of the present invention.
Figure 2:
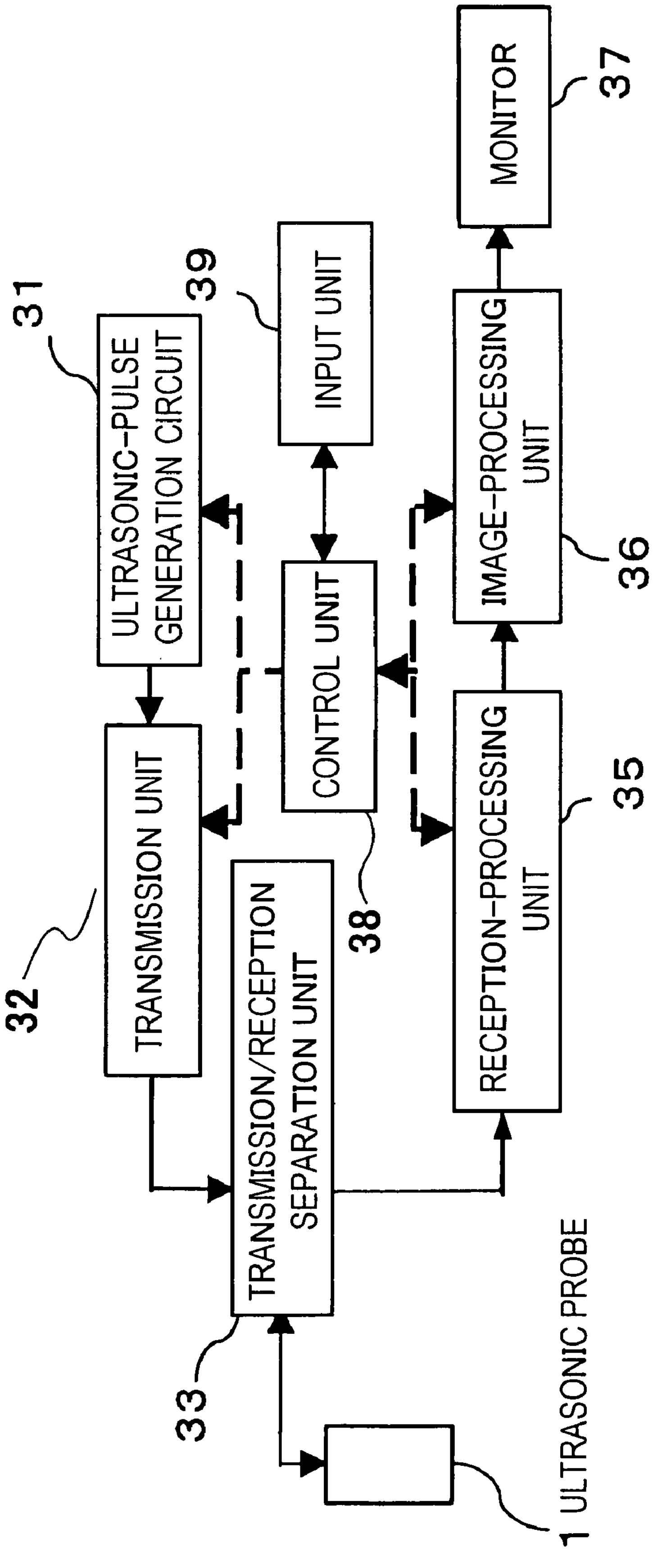
FIG. 2 shows the entire configuration of an ultrasonic diagnosing apparatus according to the embodiment of the present invention.
Figure 3:
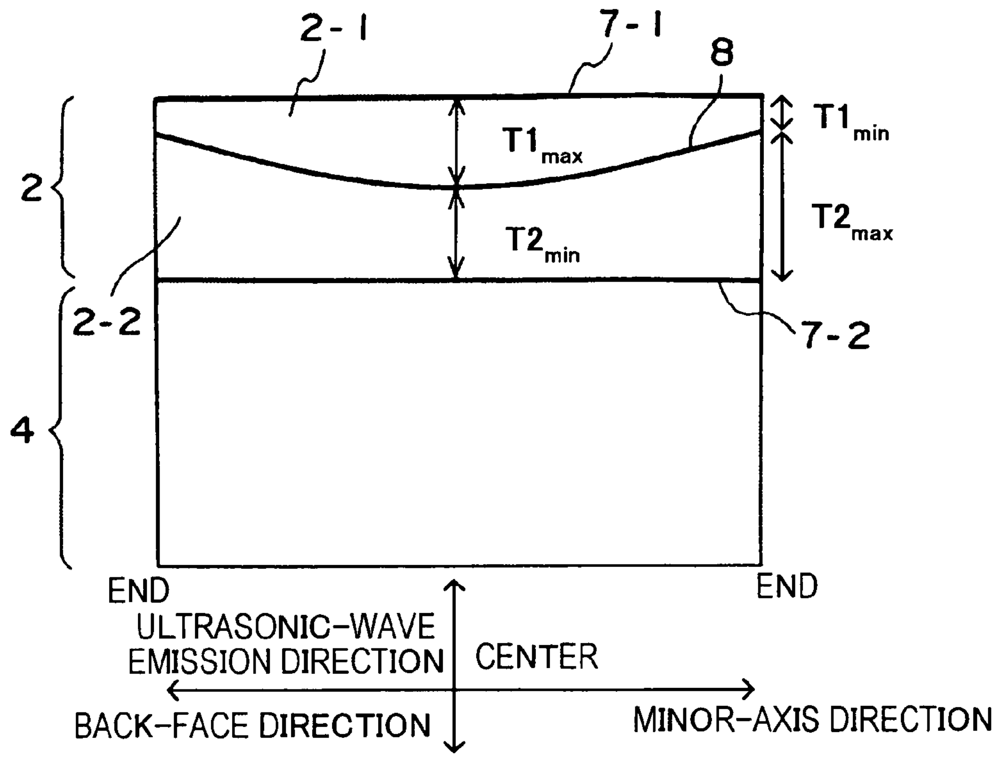
FIG. 3 is a sectional view of part relating to a piezoelectric layer according to the embodiment shown in FIG. 1.

An embodiment of the present invention will be described with reference to FIGS. 1 to 3. FIG. 1 is a perspective view of the main part of an ultrasonic probe according to the embodiment of the present invention. FIG. 2 shows the entire configuration of an ultrasonic diagnosing apparatus according to the embodiment of the present invention. FIG. 3 is a sectional view of part relating to a piezoelectric layer according to the embodiment.

In FIG. 2, an ultrasonic pulse transmitted from an ultrasonic-pulse generation circuit 31 is transmitted to a transmission unit 32 and subjected to transmission processing including transmission-focus processing, amplifying processing, and so forth therein. Then, the ultrasonic pulse is transmitted to an ultrasonic probe 1 via a transmission/reception separation unit 33. A reflective-echo signal received by the ultrasonic probe 1 is transmitted to a reception-processing unit 35 via the transmission/reception separation unit 33 and subjected to reception processing including amplifying, reception-and-phasing processing, and so forth therein. The reflective-echo signal transmitted from the reception-processing unit 35 is transmitted to an image-processing unit 36 and subjected to predetermined image-reconstruction processing therein. An ultrasonic image reconstructed by the image-processing unit 36 is displayed on a monitor 37. The above-described ultrasonic-pulse generation circuit 31, the transmission unit 32, the reception-processing unit 35, and the image-processing unit 36 are controlled based on a control instruction transmitted from a control unit 38 including a computer or the like. Further, the control unit 38 makes various settings and/or exerts control based on an instruction transmitted from an input unit 39. Further, the control unit 38 selects a configuration for scanning an ultrasonic beam by controlling an aperture-selection switch that is not shown. Further, part of the reception-processing unit 35 and the image-processing unit 36 can be formed, as a computer.

The ultrasonic probe 1 of the embodiment includes a piezoelectric layer 2, an acoustic-matching layer 3 provided on the ultrasonic-wave-emission-face side of the piezoelectric layer 2, a backing layer 4 provided on the back-face side of the piezoelectric layer 2, and an acoustic lens 5 provided on the ultrasonic-wave-emission-face side of the acoustic-matching layer 3, as shown in FIG. 1. The piezoelectric layer 2 and the acoustic-matching layer 3 are divided into a plurality of parts by a plurality of separation layers 6 arranged in the major-axis direction of the ultrasonic probe 1 so that each of the parts functions, as a transducer. Further, part of one side of the backing layer 4, the side being in contact with the piezoelectric layer 2, is divided into a plurality of parts by the plurality of separation layers 6.

Here, the acoustic lens 5 is used for performing focusing in the minor-axis direction and includes a material such as silicon rubber whose acoustic impedance is nearly equivalent to that of a body and whose sonic speed is slower than that of the body. The acoustic-matching layer 3 includes two layers. Each of the two layers functions, as a ¼-wavelength plate for a center frequency. Further, the lower layer of the acoustic-matching layer 3 includes a material such as ceramic whose acoustic impedance is lower than that of the piezoelectric layer 2. Further, the upper layer of the acoustic-matching layer 3 includes a material such as resin whose acoustic impedance is nearer to that of the body than in the case of the lower layer. The piezoelectric layer 2 includes piezoelectric-ceramic PZT, PZLT, a piezoelectric single crystal PZN-PT, PMN-PT, an organic piezoelectric material PVDF, and/or a complex piezoelectric layer including the above-described materials and a resin. The backing layer 4 includes a material that has a large ultrasonic attenuation rate and that attenuates an ultrasonic wave emitted toward the back of the piezoelectric layer 2. The separation layers 6 include a material that can significantly attenuate an ultrasonic wave (e.g., a material equivalent to a vacuum).

FIG. 3 is the sectional view of part of each of the piezoelectric layer 2 and the backing layer 4 according to the embodiment. This drawing is a sectional view of the piezoelectric layer 2 along the minor-axis direction perpendicular to the major-axis direction. The piezoelectric layer 2 has two layers including a first piezoelectric layer 2-1 and a second piezoelectric layer 2-2 that are laminated on each other. A couple of electrodes 7-1 and 7-2 are provided on an ultrasonic-wave emission face of the first piezoelectric layer 2-1 and a back face of the second piezoelectric layer 2-2. Further, a common electrode 8 is provided at the boundary of the first piezoelectric layer 2-1 and the second piezoelectric layer 2-2. The above-described electrodes 7-1, 7-2, and 8 includes metal such as silver, platinum, gold, copper, nickel, and so forth, so as to have a thickness of 10 μm or less.

Here, the first piezoelectric layer 2-1 is formed, so as to have a plane-convex shape, that is to say, the ultrasonic-wave emission face thereof is plane and the back face thereof is convex. Further, the center part thereof has the largest thickness T1max. The thickness of the first piezoelectric layer 2-1 decreases toward each of the ends. Therefore, each of the ends of the first piezoelectric layer 2-1 has the smallest thickness T1min. On the other hand, the second piezoelectric layer 2-2 is formed, so as to have a concave-plane shape, that is to say, the ultrasonic-wave emission face thereof is concave and the back face thereof is plane. Further, the center part thereof has a smallest thickness T2min. The thickness of the first piezoelectric layer 2-2 increases toward each of the ends. Therefore, each of the ends of the second piezoelectric layer 2-2 has the largest thickness T2max. Subsequently, faces that are in contact with the electrodes 7-1 and 7-2 of the piezoelectric layer 2 are formed on planes that are in parallel with each other and a boundary surface between the first piezoelectric layer 2-1 and the second piezoelectric layer 2-2 is depressed to the second-piezoelectric-layer-2-2 side. Incidentally, the piezoelectric layer 2 may be formed so that the expression T1max=T2min and the expression T1min/T2max=1/4 hold, for example.

Operations performed for making an ultrasonic diagnosis by using the above-described ultrasonic probe of the embodiment will now be described. First, the electrode 7-1 and the electrode 7-2 are grounded, and an ultrasonic transmission signal transmitted from the transmission unit 32 is applied to the common electrode 8. Here, the frequency of the transmission signal for driving the ultrasonic probe is controlled by the ultrasonic-pulse generation circuit 31. Further, the focus position of the ultrasonic beam is calculated by the control unit 38 according to the depth of a part to be measured. The part to be measured can be inputted and set by an operator through the input unit 39. An instruction is transmitted from the control means 38 to the ultrasonic-pulse generation circuit 31 and the transmission unit 32 according to the depth of the part to be measured that is set in the above-described manner, and the frequency of the transmission signal and the focus position are set. The control unit 38 transmits an instruction to the reception-processing unit 35, so as to set the frequency and focus position of a reflective-echo signal subjected to reception processing so that the frequency and focus position agree with those of the transmission signal.

Thus, the ultrasonic probe is driven, whereby an ultrasonic wave is generated in the piezoelectric layer 2 and emitted from the face thereof on the electrode 7-1 side. Here, since the piezoelectric layer 2-2 has the concave-plane shape, the piezoelectric layer 2-2 resonates at its ends at low frequencies, as is the case with the known art, and the sound pressure at low frequencies increases. On the other hand, since the piezoelectric layer 2-1 has the plane-convex shape and has a small thickness at each of its ends, the low-frequency sound pressure at each of the ends is low. As a result, by laminating the piezoelectric layer 2-1 on the piezoelectric layer 2-2, the low-frequency sound pressure at the ends can be prevented from being emphasized.

Figure 4:
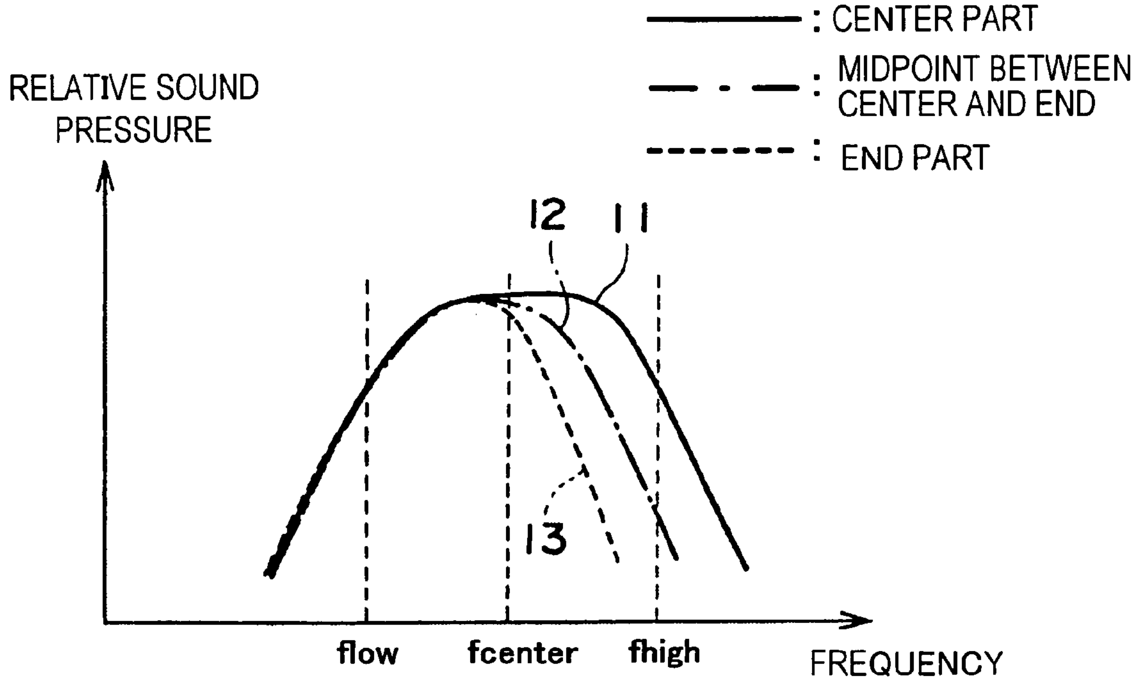
FIG. 4 shows a graph illustrating a frequency characteristic of the embodiment shown in FIG. 1.
Figure 5:
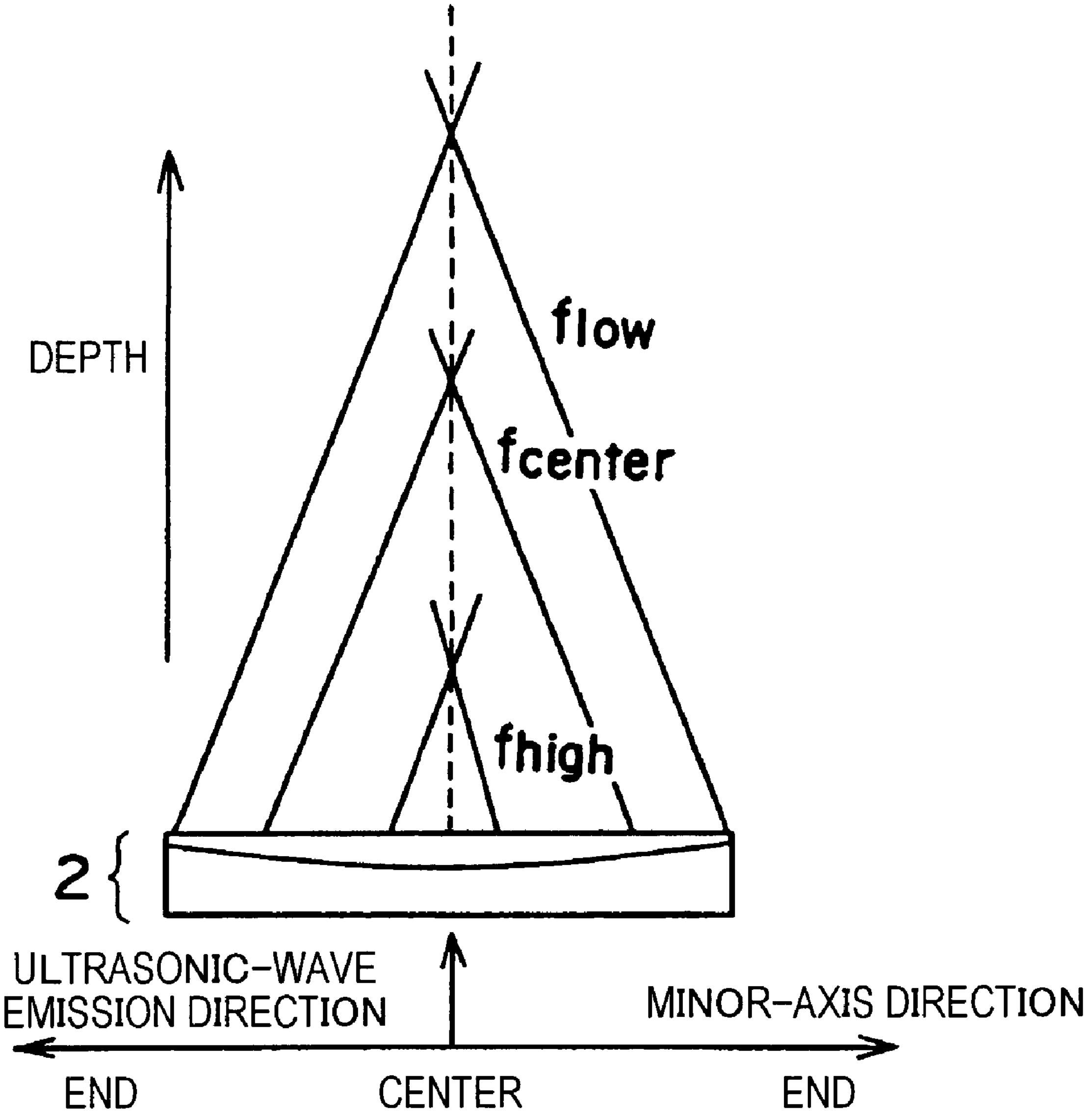
FIG. 5 is a chart showing the relationship between a frequency and a focus depth of the embodiment shown in FIG. 1.
Figure 6:
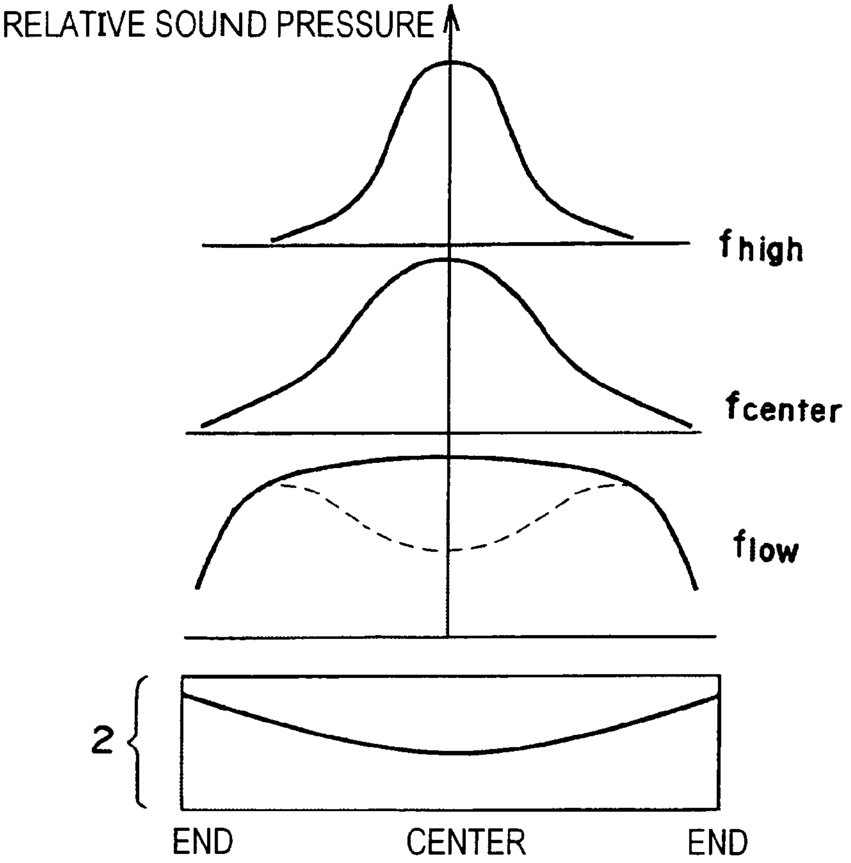
FIG. 6 is a chart illustrating the relationship between a frequency and a relative sound pressure of the embodiment shown in FIG. 1.

Here, an effect relating to the frequency characteristic of the ultrasonic probe of the embodiment will be described with reference to FIGS. 4 to 6. FIG. 4 shows the graph of the frequency characteristic of the embodiment, FIG. 5 is a chart showing the relationship between the frequency and focus depth of the embodiment, FIG. 6 is a chart illustrating the relationship between the frequency and relative sound pressure of the embodiment. In FIG. 4, the lateral axis indicates the frequency and the vertical axis indicates the relative sound pressure, a solid line 11 denotes a frequency-characteristic curve at the center in the minor-axis direction, an alternate long and short dash line 12 denotes a frequency-characteristic curve at the midpoint between the center and the end, and a dotted line 13 denotes a frequency-characteristic curve at the end. Further, in this drawing, the sign $f_{center}$ denotes the center frequency of a high frequency $f_{high}$ and a low frequency $f_{low}$. As is clear from this drawing, according to this embodiment, the high frequency $f_{high}$ resonates at the center and the low frequency $f_{low}$ resonates in an area extending from the end to the center. Subsequently, the aperture decreases at the high frequency $f_{high}$, so that a narrow beam can be generated in the neighborhood of the probe. On the other hand, the aperture increases at the low frequency $f_{low}$ that attenuates insignificantly, so that the narrow beam can be obtained at a deep part.

As a result, the function for varying an aperture according to a frequency can be obtained, as shown in FIG. 5. In FIG. 5, the lateral axis indicates the direction of the minor-axis of the piezoelectric layer 2, and the vertical axis indicates the depth thereof. Therefore, in the case of the low frequency $f_{low}$, the sound pressure at each of the ends is not higher than that at the center and the sound-pressure distribution is uniform, as shown in FIG. 6. Subsequently, the S/N ratio does not decrease and an image with high resolution can be obtained in an area extending from the neighborhood to the deep part. On the other hand, according to the known art that does not include the piezoelectric layer 2-1, low-frequency components significantly resonate at both ends in the minor-axis direction of the ultrasonic probe. Subsequently, a relative sound-pressure distribution indicated by a broken line shown in the low-frequency-$f_{low}$ characteristic chart of FIG. 6 is obtained, wherein the sound pressure at each of the ends in the minor-axis direction becomes high and the sound pressure at the center becomes low, so that the S/N ratio decreases.

Second Embodiment

Figure 7:
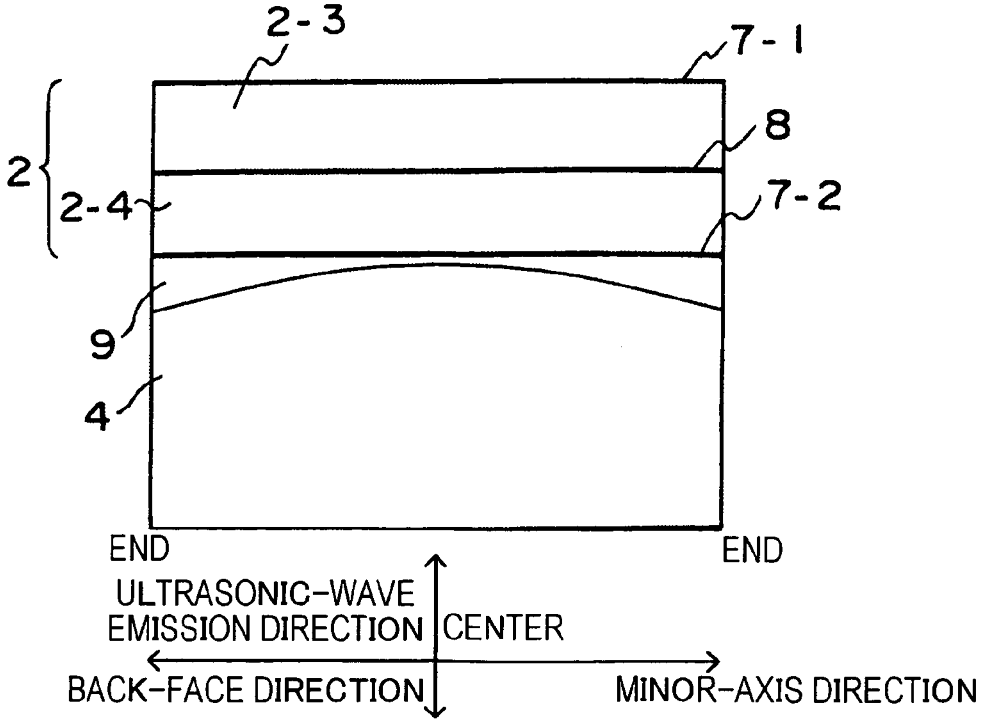
FIG. 7 is a sectional view of part relating to a piezoelectric layer according to a second embodiment of the present invention.

FIG. 7 shows a sectional view of piezoelectric-layer part of an ultrasonic probe according to a second embodiment of the present invention. The difference between the embodiment and the first embodiment is in the configuration of the two-layer configuration of the piezoelectric layer 2 and an adjustment layer 9 provided on the back face of the piezoelectric layer 2. First, the piezoelectric layer 2 includes two identically formed plane piezoelectric layers 2-3 and 2-4 that are laminated on each other. The adjustment layer 9 formed on the back face of the piezoelectric layer 2-4 includes a material whose acoustic impedance is nearly equal to that of the piezoelectric layer 2, such as metal including ceramic, aluminum, copper, and so forth. Further, the backing layer 4 includes a material whose acoustic impedance is significantly smaller than that of the adjustment layer 9 and whose attenuation rate is larger than that of the adjustment layer 9. The material includes, for example, a mixture of rubber, a resin, metal particles (tungsten particles, for example), and so forth, or a mixture of rubber, beads including a resin and gas, a micro balloon, and so forth.

According to the adjustment layer 9 of the embodiment, the surface thereof in contact with the piezoelectric layer 2-4 is plane and the opposite surface is concave. That is to say, the thickness of the adjustment layer 9 is minimized at the center thereof in the minor-axis direction and gradually increases toward each of the ends thereof. Thus, according to the embodiment, there is a large difference between the acoustic impedance of the adjustment layer 9 and that of the backing layer 4. Therefore, an ultrasonic wave is effectively reflected in the adjustment layer 9 and a frequency characteristic of the reflection depends upon the thickness. Subsequently, according to the ultrasonic probe of the embodiment, a frequency characteristic depending on the thickness of the adjustment layer 9 in the minor-axis direction can be obtained, and the effect of the frequency characteristics shown in FIGS. 4 to 6 can be obtained, as is the case with the first embodiment. That is to say, at the high frequency $f_{high}$, the response from the center part is high and the aperture is decreased so that a narrow beam can be generated in the neighborhood. Further, according to the sound pressure at the low frequency $f_{low}$, beams are uniform in the minor-axis direction for the entire aperture and focused on the deep part. As a result, an image with high resolution can be obtained in an area extending from the neighborhood to the deep part.

Third Embodiment

Figure 8:
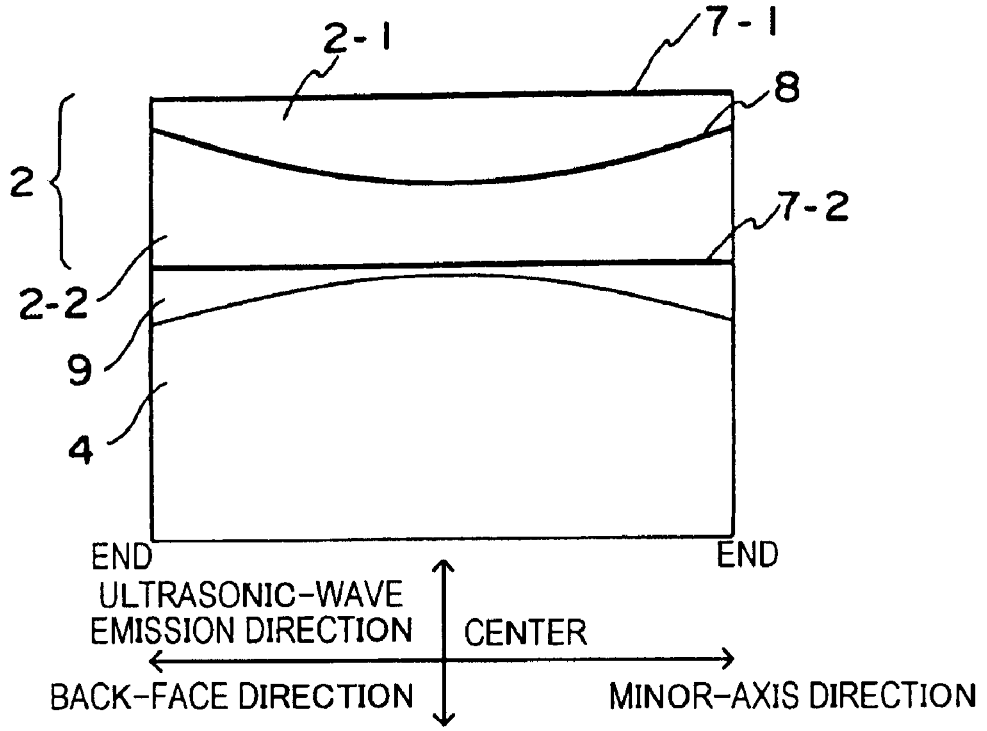
FIG. 8 is a sectional view of part relating to a piezoelectric layer according to a third embodiment of the present invention.

FIG. 8 shows a sectional view of piezoelectric-layer part of an ultrasonic probe according to a third embodiment of the present invention. The difference between the embodiment and the first embodiment is that the adjustment layer 9 is provided on the back face of the piezoelectric layer 2. In other words, the characteristic parts of the first and second embodiments are combined with each other so that both the effect of the first embodiment and that of the second embodiment can be obtained. That is to say, the sound pressure that is uniform in the minor-axis direction at low frequencies and an aperture-variable function for obtaining a beam narrower than in the past at each frequency can be achieved.

Fourth Embodiment

Figure 9:
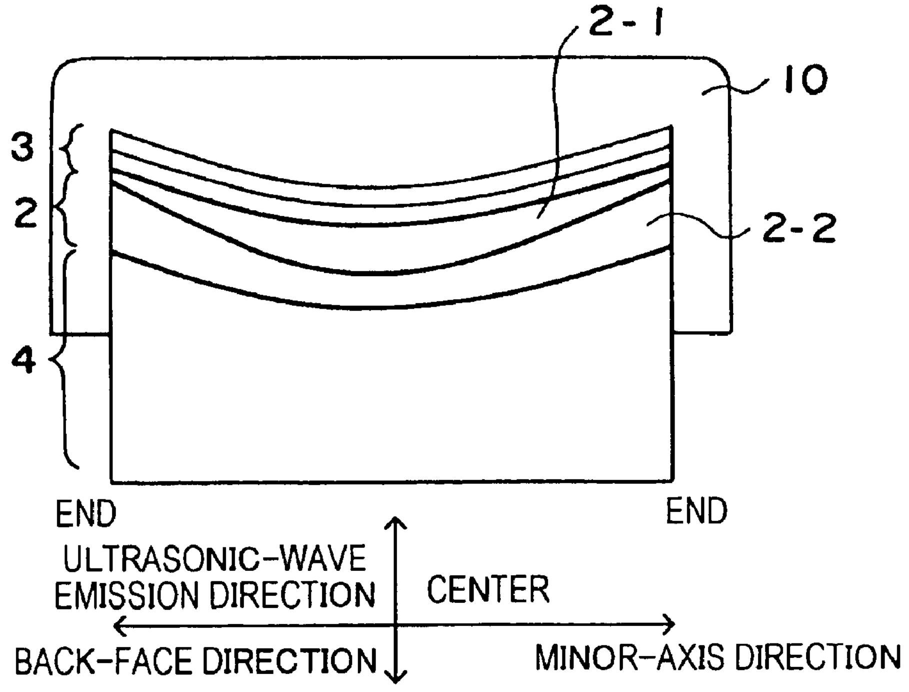
FIG. 9 is a sectional view of part relating to a piezoelectric layer according to a fourth embodiment of the present invention.

FIG. 9 shows a sectional view of piezoelectric-layer part of an ultrasonic probe according to a fourth embodiment of the present invention. The difference between the embodiment and the first embodiment is that the sectional shape of the piezoelectric layer 2 is concave, as shown in this drawing and the section of the acoustic-matching layer 3 is concave so that the section of the acoustic-matching layer 3 matches with that of the piezoelectric layer 2. That is to say, the piezoelectric layer 2 is formed so that the ultrasonic-wave emission face and back face thereof are concave and in parallel with each other. The thickness of the piezoelectric layer 2-1 on the emission side is maximized at the center thereof, gradually decreased toward each of the ends thereof, and minimized at each of the ends. On the other hand, the thickness of the piezoelectric layer 2-2 on the back-face side is minimized at the center thereof and increases toward both the ends thereof so that the thickness is maximized at each of the ends. Further, the backing layer 4 is formed, so as to match with the concave back face of the piezoelectric layer 2-2. Further, the acoustic lens is removed and a cover member 10 is formed by using a material whose acoustic impedance and sonic speed are nearly equivalent to those of the body of the patient. For example, the material includes polyurethane, flux, butadiene rubber, polyether block amide, and so forth. Further, the cover member 10 has a concave shape, so that the cover member 10 is in good contact with the body. According to the configuration, the minor-axis variable focus function is achieved and a beam can be focused by the concave piezoelectric layer 2. As a result, since the beam can be focused without using the acoustic lens, attenuation of an ultrasonic wave decreases and a highly sensitive image can be obtained.

Fifth Embodiment

Figure 10:
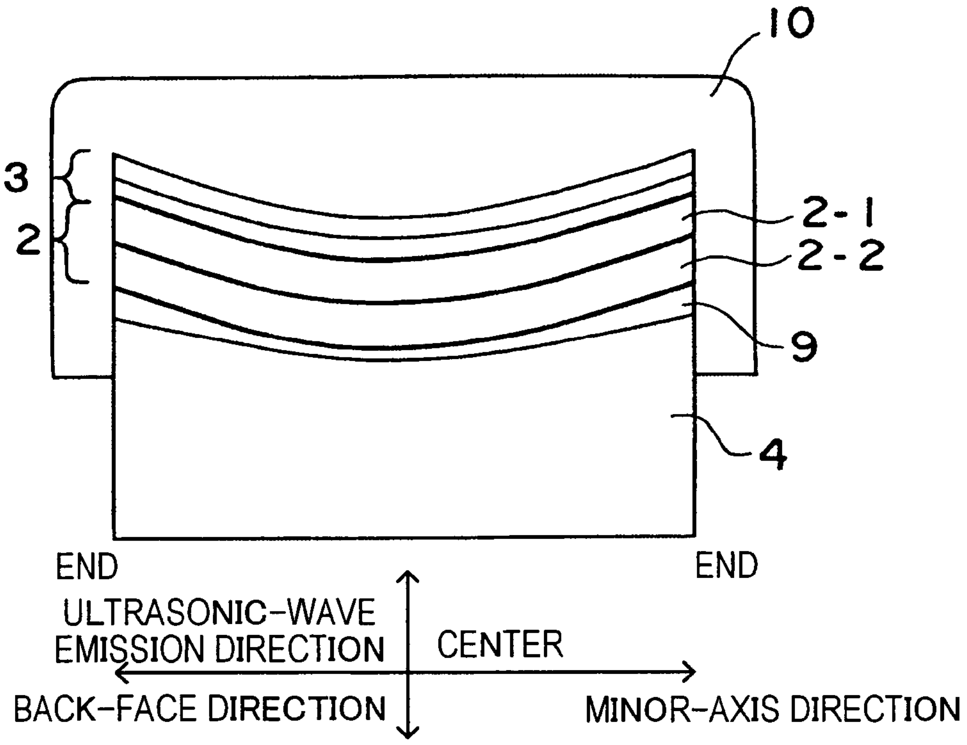
FIG. 10 is a sectional view of part relating to a piezoelectric layer according to a fifth embodiment of the present invention.

FIG. 10 shows a sectional view of piezoelectric-layer part of an ultrasonic probe according to a fifth embodiment of the present invention. The difference between the embodiment and the second embodiment is that the sectional shape of the piezoelectric layer 2 is concave, as shown in this drawing and the section of the acoustic-matching layer 3 is concave so that section of the acoustic-matching layer 3 matches with that of the piezoelectric layer 2. That is to say, the piezoelectric layer 2 is formed, as a concave, where the ultrasonic-wave emission face and back face thereof are in parallel with each other. Further, the adjustment layer 9 is provided on the back face of the piezoelectric layer 2, where the thickness of the adjustment layer 9 is minimized at the center thereof, increased toward both the ends thereof, and maximized at the ends. Subsequently, a frequency characteristic depending upon the thickness can be obtained. Further, the cover member 10 is provided in place of the acoustic lens. The materials of the adjustment layer 9 and the cover member 10 are the same as those in the fourth embodiment. According to the fifth embodiment, the minor-axis variable focus function is obtained and a beam can be focused by the concave piezoelectric layer 2. As a result, the beam can be focused without using the acoustic lens, attenuation of an ultrasonic wave decreases, and a highly sensitive image can be obtained.

Sixth Embodiment

Figure 11:
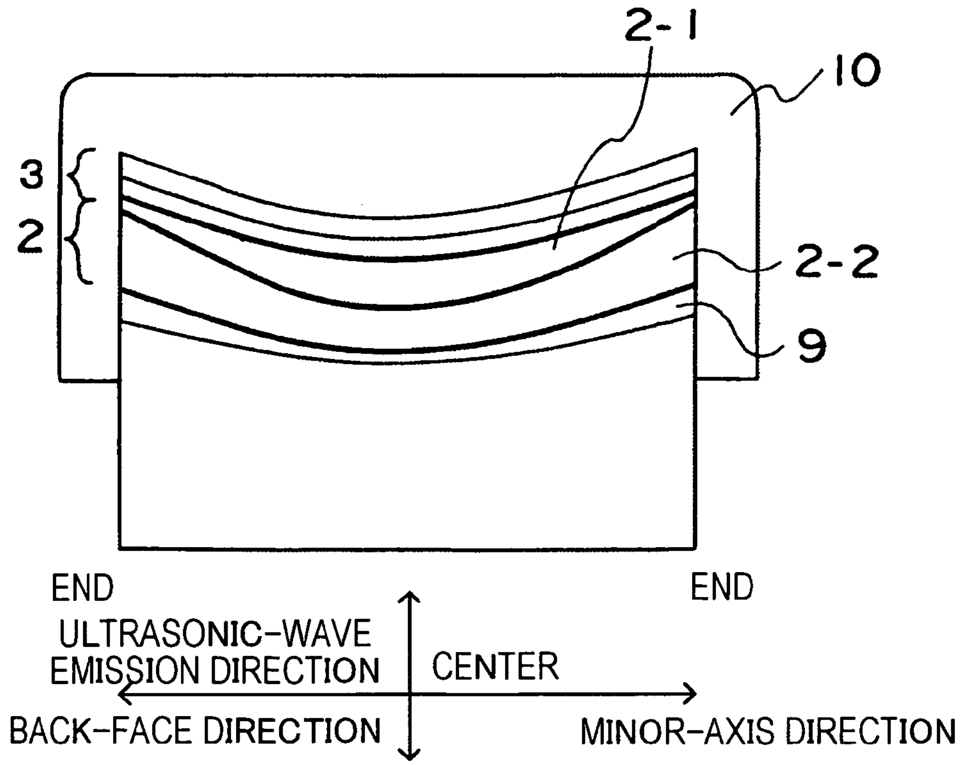
FIG. 11 is a sectional view of part relating to a piezoelectric layer according to a sixth embodiment of the present invention.

FIG. 11 shows a sectional view of piezoelectric-layer part of an ultrasonic probe according to a sixth embodiment of the present invention. The embodiment is a combination of the fourth and fifth embodiments and an effect including the effects of the above-described two embodiments can be obtained. That is to say, the sound pressure that is uniform in the minor-axis direction at low frequencies and an aperture-variable function for obtaining a beam narrower than in the past at each frequency can be achieved. Further, since the lens is not used, the attenuation decreases and a highly sensitive image can be obtained.

Seventh Embodiment

Figure 12:
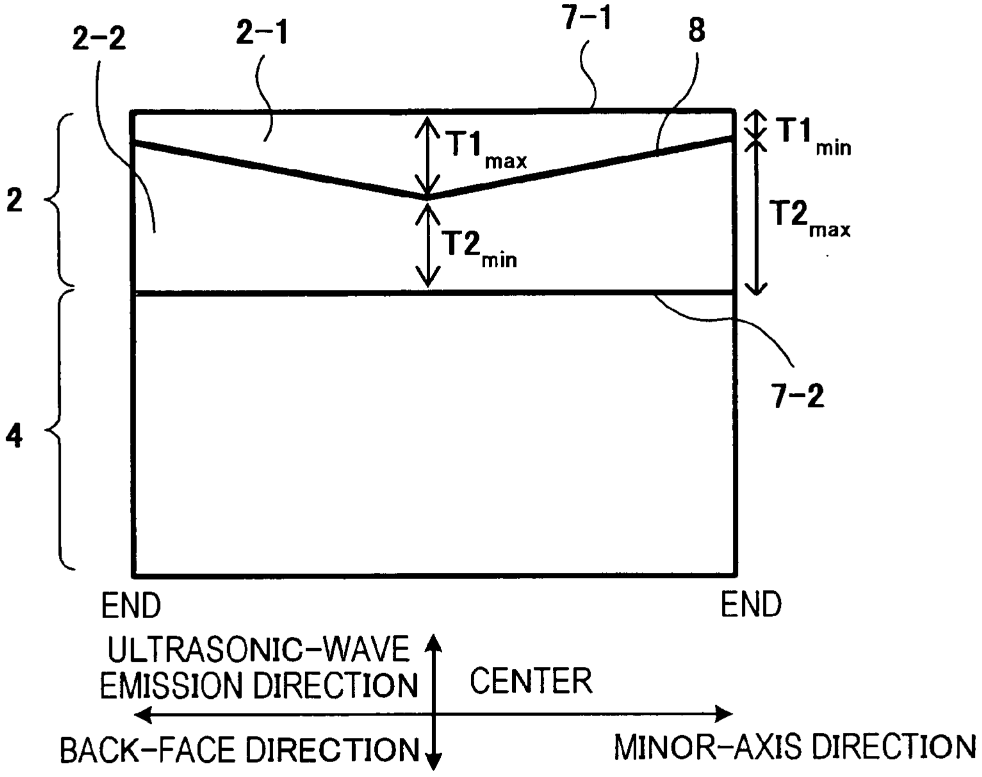
FIG. 12 is a sectional view of part relating to a piezoelectric layer according to a seventh embodiment of the present invention.

FIG. 12 shows a sectional view of piezoelectric-layer part of an ultrasonic probe according to a seventh embodiment of the present invention. According to the embodiment, the first piezoelectric layer 2-1 has a plane-convex shape, where the ultrasonic-wave emission face thereof is plane and the back face thereof is convex, as is the case with the embodiment shown in FIG. 3. Further, the second piezoelectric layer 2-2 has a concave-plane shape, where the ultrasonic-wave emission face thereof is concave and the back face thereof is plane. The boundary surface between the first piezoelectric layer 2-1 and the second piezoelectric layer 2-2 is formed, as a crest whose ridge line corresponds to the center part in the minor-axis direction. Further, the common electrode 8 is formed on the boundary surface.

According to the embodiment, the sound pressure at low frequencies of each of the ends is lower than that of the center part and the sound-pressure distribution is uniform, as is the case with the embodiment shown in FIG. 3. Therefore, the S/N ratio does not decrease and a high-resolution image can be obtained in an area extending from the neighborhood to the deep part.

Further, in this embodiment, the adjustment layer 9 shown in FIG. 7 can also be provided on the back-face side of the second piezoelectric layer 2-2.

Eighth Embodiment

Figure 13:
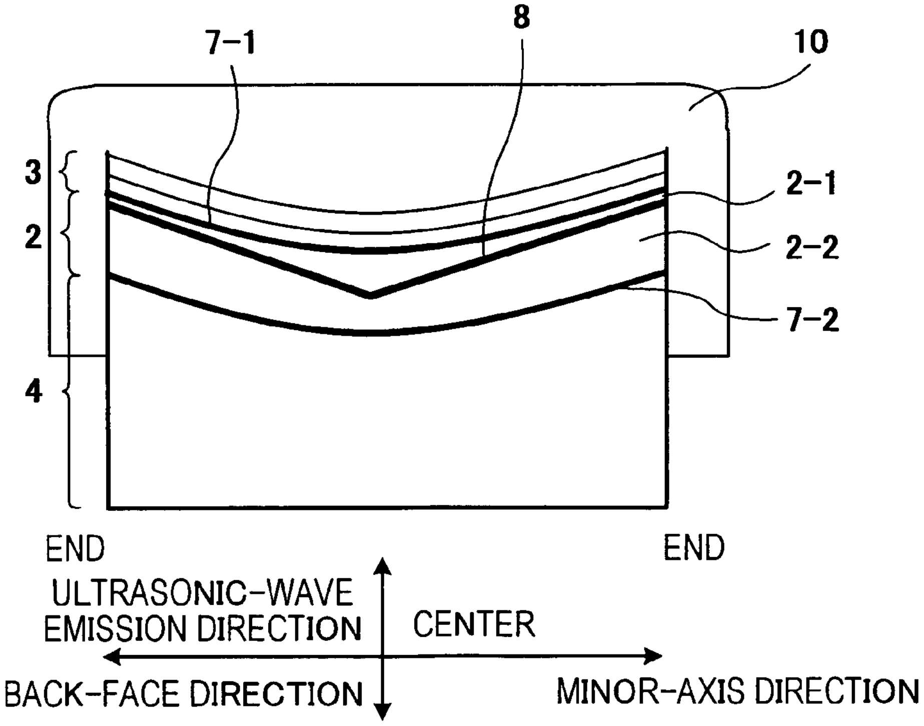
FIG. 13 is a sectional view of part relating to a piezoelectric layer according to an eighth embodiment of the present invention.

FIG. 13 shows a sectional view of piezoelectric-layer part of an ultrasonic probe according to an eighth embodiment of the present invention. This embodiment is achieved by modifying the configuration of the first and second piezoelectric layers 2-1 and 2-2 of the embodiment shown in FIG. 11 so that the boundary surface therebetween is formed, as a crest whose ridge line corresponds to the center part in the minor-axis direction, as is the case with FIG. 12. Accordingly, the sound pressure that is uniform in the minor-axis direction at low frequencies and the aperture-variable function for generating a beam narrower than in the past at each frequency can also be achieved, as is the case with the embodiment shown in FIG. 11. Further, since the lens is not used, the attenuation is decreased and a high-resolution image can be obtained.

Further, according to the embodiment, the adjustment layer 9 shown in FIG. 7 can be provided on the back-face side of the second piezoelectric layer 2-2.

Ninth Embodiment

Figure 14:
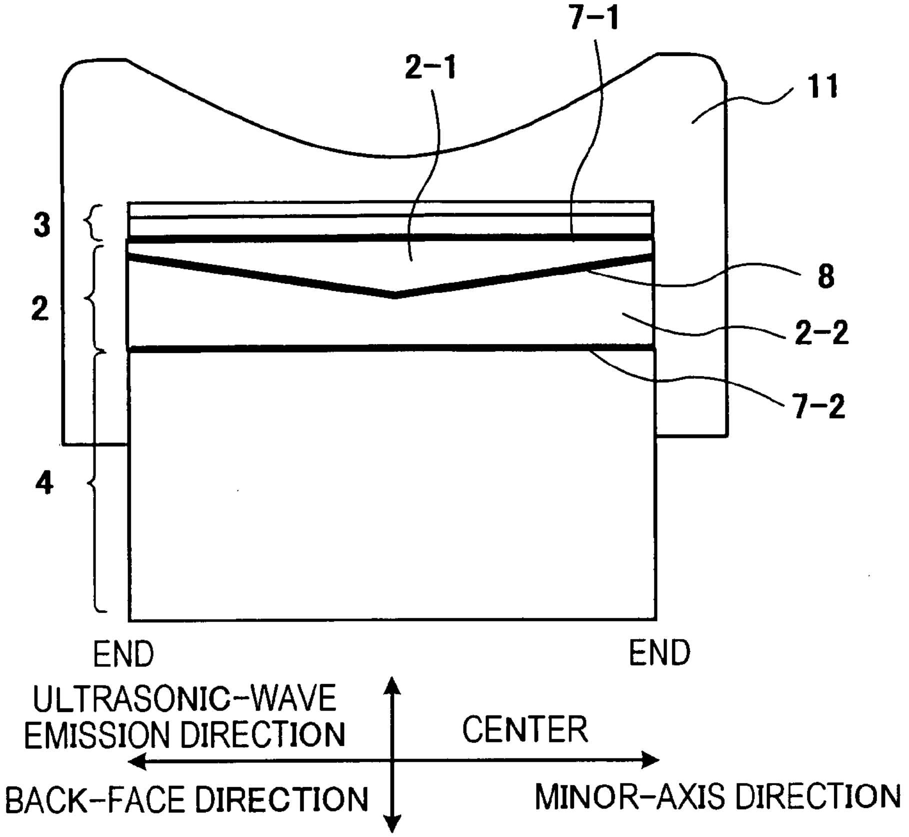
FIG. 14 is a sectional view of part relating to a piezoelectric layer according to a ninth embodiment of the present invention.

FIG. 14 shows a sectional view of piezoelectric-layer part of an ultrasonic probe according to a ninth embodiment of the present invention. In this embodiment, the acoustic-matching layer 3 is provided on the ultrasonic-wave emission side of the piezoelectric layer 2 according to the embodiment shown in FIG. 12 and an acoustic lens 11 achieved by modifying the shape of the acoustic lens 5 into a concave is provided. According to the concave acoustic lens 11, there is a difference between the sound pressure of thin part thereof and that of thick part thereof, so that an ultrasonic beam becomes narrower in the minor-axis direction and an ultrasonic beam at a low frequency becomes narrow due to the configuration of the piezoelectric layer 2 added thereto. Subsequently, it becomes possible to achieve an aperture-variable function for a beam narrower than in the past at each frequency.

The concave acoustic lens 11 can be used for other embodiments. Further, in this embodiment, the adjustment layer 9 shown in FIG. 7 can be provided on the back-face side of the second piezoelectric layer 2-2.

Tenth Embodiment

Figure 15:
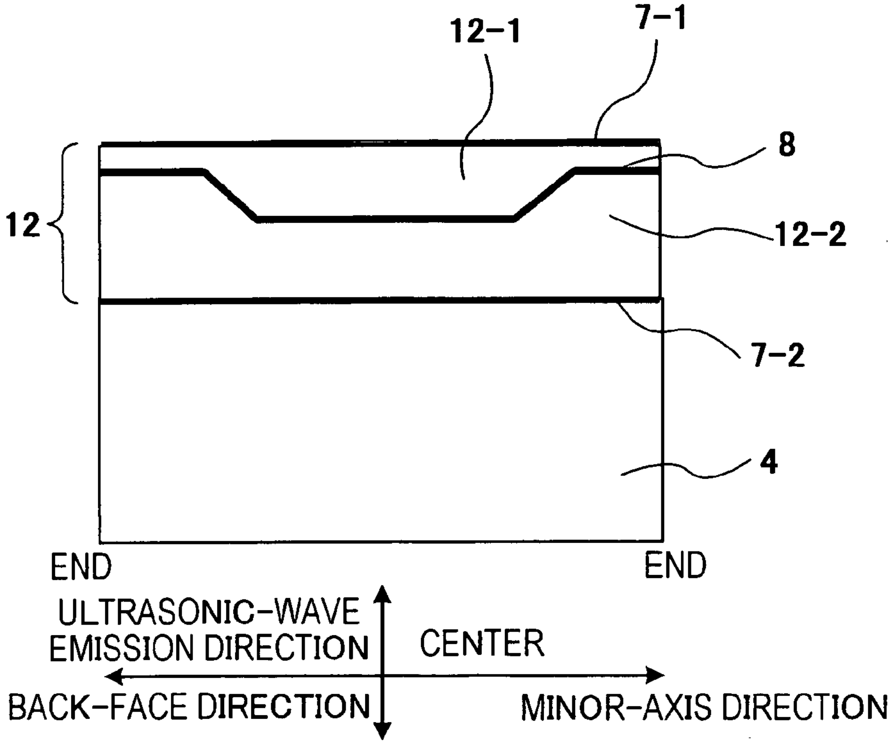
FIG. 15 is a sectional view of part relating to a piezoelectric layer according to a tenth embodiment of the present invention.

FIG. 15 shows a sectional view of piezoelectric-layer part of an ultrasonic probe according to a tenth embodiment of the present invention. According to the embodiment, a first piezoelectric layer 12-1 has a plane-convex shape, where the ultrasonic-wave emission face thereof is plane and the back face thereof is convex, as is the case with the embodiment shown in FIG. 3. Further, a second piezoelectric layer 12-2 has a concave-plane shape, where the ultrasonic-wave emission face thereof is concave and the back face thereof is plane. The boundary surface between the first piezoelectric layer 12-1 and the second piezoelectric layer 12-2 includes a plane part that is provided at the center part in the minor-axis direction and projected to the second-piezoelectric-layer side, and a plane part on each of both the sides thereof, where the plane parts are projected to the first-piezoelectric-layer side. The common electrode 8 is provided on the boundary surface.

According to the embodiment, at low frequencies, the sound pressure at each of the ends is not higher than that at the center part and the sound-pressure distribution is uniform, as is the case with the embodiment shown in FIG. 3. Subsequently, the S/N ratio does not decrease and an image with high resolution can be obtained in an area extending from the neighborhood to the deep part. Further, in this embodiment, the adjustment layer 9 shown in FIG. 7 can also be provided on the back-face side of the second piezoelectric layer 12-2.

Eleventh Embodiment

Figure 16:
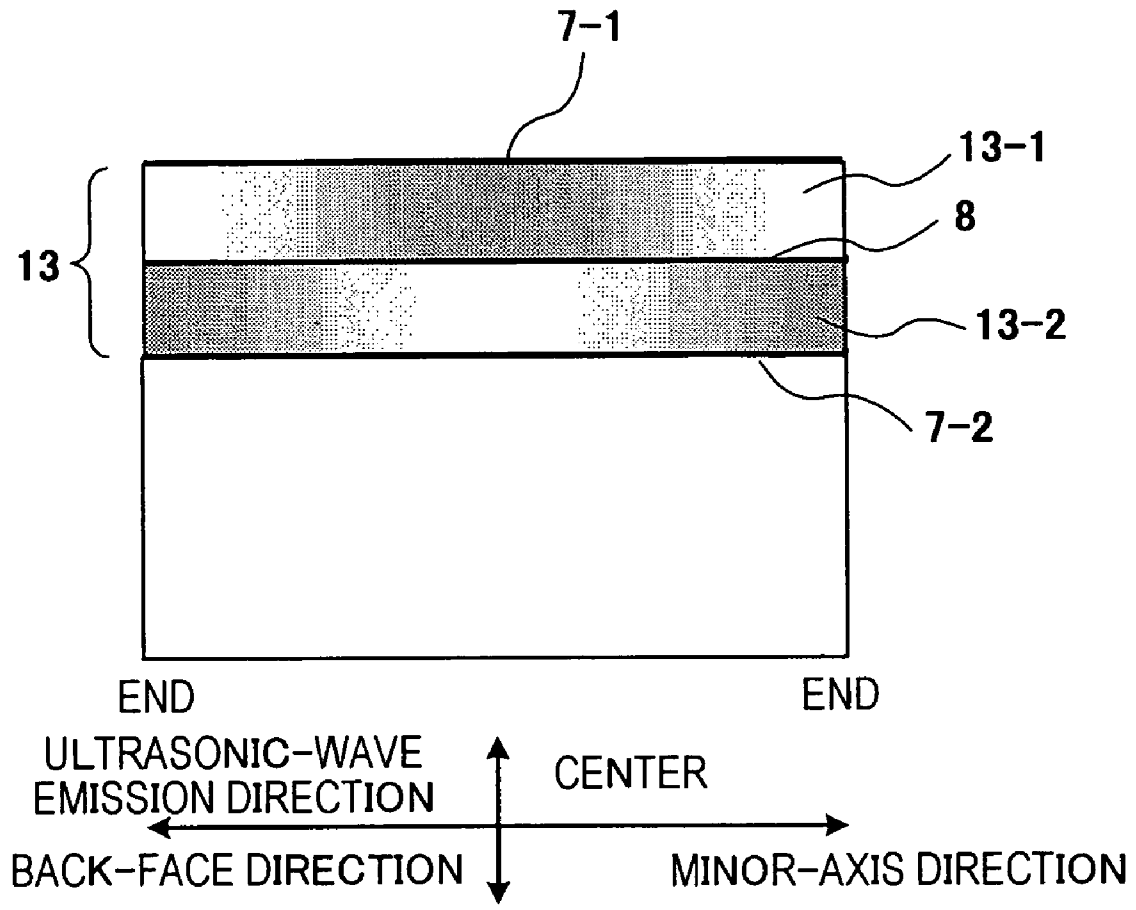
FIG. 16 is a sectional view of part relating to a piezoelectric layer according to an eleventh embodiment of the present invention.

FIG. 16 shows a sectional view of piezoelectric-layer part of an ultrasonic probe according to an eleventh embodiment of the present invention. In this embodiment, a piezoelectric layer 13 includes a first piezoelectric layer 13-1 and a second piezoelectric layer 13-2, where each of the piezoelectric layers has a predetermined thickness. The density of a piezoelectric material used for the first piezoelectric layer 13-1 gradually decreases from the center part in the minor-axis direction toward the end. The density of the piezoelectric material used for the second piezoelectric layer gradually increases from the center part in the minor-axis direction toward the end. Subsequently, the frequency constant of the first piezoelectric layer 13-1 increases from the center part toward both the ends and the frequency constant of the second piezoelectric layer 13-2 decreases from the center part toward both the ends, so that the frequency-response characteristic in the minor-axis direction can be adjusted. The density of the piezoelectric material can be adjusted by modifying the porosity of itself, such as the above-described piezoelectric ceramic. Further, the density can be modified by mixing a resin or the like into the piezoelectric material.

According to the embodiment, it becomes possible to achieve a sound-pressure distribution that is uniform in the minor-axis direction at low frequencies and an aperture-variable function for obtaining a narrow beam in a wide frequency band. Further, in this embodiment, the adjustment layer 9 shown in FIG. 7 is provided on the back-face side of the second piezoelectric layer 13-2, the piezoelectric layer is formed, as a concave, as shown in FIG. 9, and the concave acoustic lens 11 shown in FIG. 14 is provided. That is to say, the characteristic technology of the other embodiments can be used, as required.

Further, the same effect can be obtained by adjusting the elastic constant of the piezoelectric material instead of adjusting the density of the piezoelectric material, as in the above-described embodiment. In that case, the elastic constant of the first piezoelectric layer 13-1 is minimized at the center in the minor-axis direction and gradually increases toward the end. The elastic constant of the second piezoelectric layer is maximized at the center in the minor-axis direction and gradually decreases toward the end.

As has been described, according to each of the embodiments of the present invention, the frequency response characteristic varies from the center part in the minor-axis direction towards the ends so that a wide band ranging from a low-frequency band to a high-frequency band is achieved at the center part and a narrow band wherein a high-frequency response decreases is achieved at the end. Further, at low frequencies, the sound pressure at each of the ends does not increase so that a uniform sound pressure can be obtained in the area ranging from the center part to the end. Further, at high frequencies, a response from the center part increases, so that focus is achieved in the neighborhood of the probe. At low frequencies, focus is achieved at the deep part due to responses for the entire aperture, so that a high-resolution image can be obtained.

The invention claimed is:

1. An ultrasonic-diagnosing apparatus including an ultrasonic probe having a plurality of transducers, transmission means for transmitting an ultrasonic signal for driving the transducers of the ultrasonic probe, reception-processing means for performing reception processing for a reflective-echo signal received by the ultrasonic probe, image-processing means for reconstructing an ultrasonic image based on the reflective-echo signal processed by the reception-processing means, and image-display means for displaying the ultrasonic image reconstructed by the image-processing means, wherein the ultrasonic probe comprises an array of a plurality of ultrasonic transducers, wherein a piezoelectric layer of each of the ultrasonic transducers comprises a first piezoelectric layer which has one face serving as an ultrasonic-wave emission face, a second piezoelectric layer which is laminated on a face of the first piezoelectric layer opposite to the ultrasonic-wave emission face, a common electrode which is provided at a laminate boundary surface between the first piezoelectric layer and the second piezoelectric layer and to which the ultrasonic signal is transmitted, a first ground electrode which is provided on the ultrasonic-wave emission face to the first piezoelectric layer, and a second ground electrode which is provided on a back face of the second piezoelectric layer on the side opposite to the laminate boundary surface, and wherein, the ultrasonic-wave emission face and the back face are formed as either a plane face or a curved face and arranged in parallel with each other, a thickness of the first piezoelectric layer in a minor axis direction perpendicular to a major axis direction of the ultrasonic transducer is formed largest at a center part and smallest at each end, and a thickness of the second piezoelectric layer in the minor axis direction is formed smallest at a center part and largest at each end.

2. The ultrasonic-diagnosing apparatus according to claim 1, wherein an adjustment layer including a material whose acoustic impedance is nearly equivalent to an acoustic impedance of a piezoelectric material used for the piezoelectric layer is provided on the side of the back face and wherein the thickness of the adjustment layer in the minor-axis direction gradually increases from the center part to the end.

3. The ultrasonic-diagnosing apparatus according to claim 1, further comprising an acoustic matching layer provided on the side of the ground electrode of the first piezoelectric layer and a backing layer provided on the side of the ground electrode of the second piezoelectric layer.

4. The ultrasonic-diagnosing apparatus according to claim 1, wherein in the case of the ultrasonic-wave emission face and the back face are each formed a plane face and arranged in parallel each other, a boundary surface between the first piezoelectric layer and the second piezoelectric layer is formed as a crest whose ridge line corresponds to the center part in the minor-axis direction.

5. The ultrasonic-diagnosing apparatus according to claim 1, wherein in the case of the ultrasonic-wave emission face and the back face are formed a plane face arranged in parallel each other, a boundary surface between the first piezoelectric layer and the second piezoelectric layer comprises a plane part that is provided at the center part in the minor-axis direction and that is projected to the second-piezoelectric-layer side, and a plane part that is provided at each of both the ends, where the plane parts are projected to the first-piezoelectric-layer side.

6. The ultrasonic-diagnosing apparatus according to claim 1, wherein in the case of the ultrasonic-wave emission face and the back face are formed a curved face and arranged in parallel each other, the ultrasonic-wave emission face is concave, the back face is convex, and a boundary surface between the first piezoelectric layer and the second piezoelectric layer has a curvature larger than the curvature of the ultrasonic-wave emission face.

7. The ultrasonic-diagnosing apparatus according to claim 1, wherein in the case of the ultrasonic-wave emission face and the back face are formed a curved face and arranged in parallel each other, the ultrasonic-wave emission face is concave, the back face is convex, and a boundary surface between the first piezoelectric layer and the second piezoelectric layer is formed as a crest whose ridge line corresponds to the center part in the minor-axis direction.

* * * * *